Feb. 2, 1960 H. C. SWIM Plant Pat. 1,903
ROSE PLANT
Filed Dec. 29, 1958
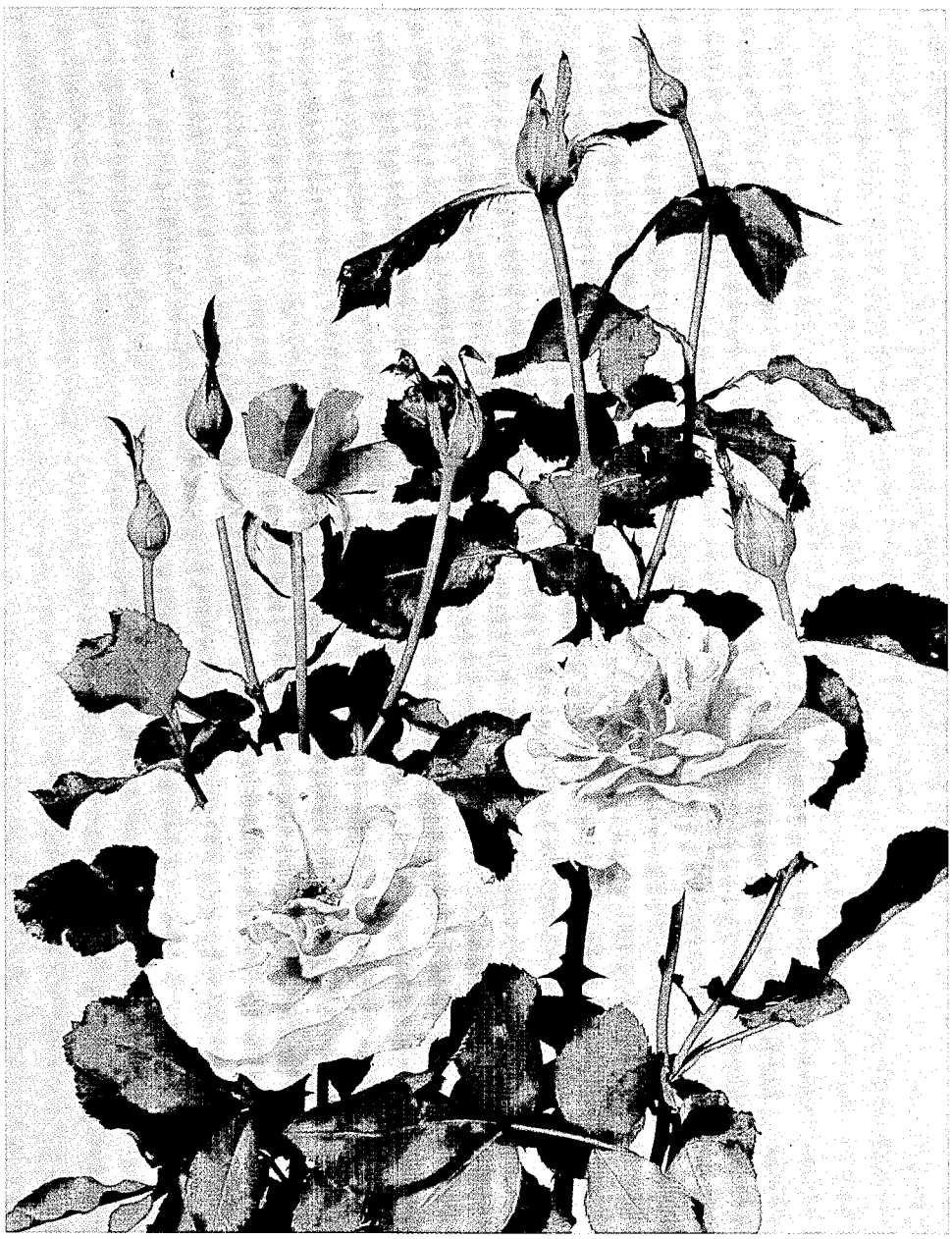
Inventor.
H. C. Swim
By: Robb & Robb
Attorneys.

United States Patent Office

Plant Pat. 1,903
Patented Feb. 2, 1960

1,903

ROSE PLANT

Herbert C. Swim, Ontario, Calif., assignor to Armstrong Nurseries, Inc., Ontario, Calif., a corporation of California Application December 29, 1958, Serial No. 783,630

1 Claim. (Cl. 47—61)

The present invention relates to a new and distinct variety of rose plant of the class falling between the hybrid tea and floribunda classes, which was originated by me by crossing the variety "Fandango" (Plant Patent No. 894) with the variety "Roundelay" (Plant Patent No. 1,280).

The general objective of this breeding was to produce a new rose variety, the plant of which has the vigor and disease resistance of the pollen parent, "Roundelay," and the attractive and glossy foliage of the seed parent "Fandango," combined with a floriferousness equal to or greater than that of either parent, with the flowers borne on stems of medium length or longer, and in an upright manner, and flowers of moderately double type with the size and form of those of "Fandango," and of a color of any attractive type. This general objective was achieved in the new variety, along with other desirable improvements, as evidenced by the following unique combination of characteristics which are outstanding in the new variety and which distinguish it from its parents, as well as from all other varieties of which I am aware:

(1) A very vigorous, much-branched and fast-breaking plant habit;

(2) Attractive and disease-resistant foliage of from medium to large size;

(3) A floriferousness at least as good as, and probably slightly better than, either "Roundelay" or "Fandango";

(4) A habit of bearing flowers on stems of medium length, with the flowers borne sometimes singly and sometimes in small clusters;

(5) An attractive ovoid to urn-shaped bud form, said buds opening to a well-formed, high-centered, double flower of medium petalage;

(6) A flower size about equal to that of "Fandango";

(7) A better-than-average flower petal substance, making the flower quite long-lasting when cut, despite the medium number of petals; and (8) A general color tonality of the flowers of light pink on the inner surface of the petals, with dark pink on the reverse surface of the petals.

In comparison with its seed parent, "Fandango," the new variety is more vigorous; and the flower color is light pink on the inside of the petals and dark pink on the reverse side, whereas the flower color of "Fandango" is a brilliant light red.

As compared with its pollen parent, "Roundelay," the new variety has larger, less double, but better shaped flowers; and the flowers are light pink on the inside of the petals and dark pink on the reverse side, whereas those of "Roundelay" are dark red.

Asexual reproduction of my new variety by budding, as performed at Ontario, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), except where general color terms of ordinary dictionary significance are obvious:

Type: Bush; outdoor; seedling; for cut flowers and for garden decoration.

Class: Between hybrid tea and floribunda.

Breeding: Seedling.

*Seed parent.*—"Fandango."

*Pollen parent.*—"Roundelay."

Propagation: Holds its distinguishing characteristics through succeeding propagations by budding.

*Flower*

Locality where grown and observed: Ontario, California.

Flowers borne: Sometimes singly and sometimes from 2 to 5 or more to stem; in irregular clusters; on strong stems of medium length.

Quantity of bloom: Abundant, outdoors.

Continuity: Nearly continuous during growing season.

Fragrance: Slight.

Bud:

*Peduncle.*—Average length; from average caliper to heavy; erect; usually smooth; with from none to few stipitate glands. Color—near Grape Green, Plate XLI (Ridgway), overlaid with near Verona Brown, Plate XXIX (Ridgway) on side exposed to the sun.

*Before calyx breaks.*—Size—medium. Form—medium length; ovoid.

*As calyx breaks.*—Color—between Turkey Red, Plate 721/3, page 94 (Wilson) and Cardinal Red, Plate 822/3, page 168 (Wilson).

*Sepals.*—Inner surface—with fine, woolly tomentum. Outer surface—usually smooth. Margins of alternate sepals—lined with fine, woolly tomentum. Margins of other sepals—lined with stipitate glands and slender foliaceous appendages, with foliaceous parts sometimes extending beyond the tip equal to ⅓ or more of its length.

*As first petal opens.*—Size—average. Form—medium length; from ovoid to urn-shaped. Color: outside—near Turkey Red, Plate 721/3, page 94 (Wilson), usually blending with near Signal Red, Plate 719/3, page 93 (Wilson) toward base of petal, with small area at base of petal near Empire Yellow, Plate 603, page 66 (Wilson); inside—near Geranium Lake, Plate 20/2, page 20 (Wilson), usually blending with near Vermilion, Plate 18/1, page 18 (Wilson) toward base of petal, and with small area at base of petal near Empire Yellow, Plate 603, page 66 (Wilson).

*Opening.*—Opens up well; is not retarded from opening by cold, hot, wet or dry weather.

Bloom:

*Size (when fully open).*—From average to large; from 4 inches to 4¾ inches.

*Petalage.*—Double; from 25 to 35 petals, often with from 8 to 14 petaloids; arranged regularly.

*Form.*—High-centered and somewhat globular at first, but becoming from open to cupped; petals at first being somewhat cupped, but later becoming more loosely cupped at maturity; lateral margins of inner petals usually reflexed from ⅔ to ¾ of petal length; lateral margins of intermediate and outer petals usually slightly reflexed the entire petal length; tip of petal usually flat.

Petals:

*Texture.*—Thick; leathery. Inside—velvety. Outside—slightly satiny.

*Shape.*—Outer—broadly obovate, with apex flat. Intermediate—obovate, with apex from rounded to flat and with one or two notches. Inner—narrowly obovate, with apex rounded and sometimes with one or two notches.

This description of a newly opened flower was made from a rose grown outdoors in the month of October at Ontario, California:

*Color.*—Outer petal: outside surface—near Rose Madder, Plate 23/1, page 23 (Wilson), usually blending with near Geranium Lake, Plate 20/1, page 20 (Wilson) toward base of petal, with small area at base of petal near Empire Yellow, Plate 603, page 66 (Wilson); inside surface—near Carmine, Plate 21/2, page 21 (Wilson), usually blending with near Vermilion, Plate 18/2, page 18 (Wilson) toward base of petal, with small area at base of petal near Empire Yellow, Plate 603, page 66 (Wilson). Intermediate petal: outside surface—near Crimson, Plate 22/1, page 22 (Wilson), usually blending with near Geranium Lake, Plate 20/1, page 20 (Wilson) toward base of petal, with small area at base of petal near Empire Yellow, Plate 603, page 66 (Wilson); inside surface—near Carmine, Plate 21/1, page 21 (Wilson), usually blending with near Vermilion, Plate 18/2, page 18 (Wilson) toward base of petal, with small area at base of petal near Empire Yellow, Plate 603, page 66 (Wilson). Inner petal: outside surface—near Crimson, Plate 22, page 22 (Wilson), usually blending with near Geranium Lake, Plate 20, page 20 (Wilson) toward base of petal, with small area at base of petal near Empire Yellow, Plate 603, page 66 (Wilson); inside surface—near Carmine, Plate 21/1, page 21 (Wilson), usually blending with near Vermilion, Plate 18/1, page 18 (Wilson) toward base of petal, with small area at base of petal near Empire Yellow, Plate 603, page 66 (Wilson).

This description was made from a rose that was open for 3 days outdoors in the month of October at Ontario, California:

*Color.*—Outer petal: outside surface—near Rose Madder, Plate 23/2, page 23 (Wilson), with small area at base of petal near Straw Yellow, Plate 604/1, page 67 (Wilson); inside surface—near Rose Madder, Plate 23/3, page 23 (Wilson), with small area at base of petal near Straw Yellow, Plate 604/1, page 67 (Wilson). Inner petal: outside surface—near Rose Madder, Plate 23/1, page 23 (Wilson), with small area at base of petal near Empire Yellow, Plate 603/1, page 66 (Wilson); inside surface—near Rose Madder, Plate 23/2, page 23 (Wilson), with small area at base of petal near Empire Yellow, Plate 603/1, page 66 (Wilson).

*General color effect.*—Newly opened flower—between Carmine, Plate 21/1, page 21 (Wilson) and Carmine, Plate 21/2, page 21 (Wilson). 3-days open—between Rose Madder, Plate 23/2, page 23 (Wilson) and Rose Madder, Plate 23/3, page 23 (Wilson).

*Behavior.*—Drop off cleanly; not particularly affected by cold, hot, wet or dry weather.

*Flower longevity.*—On bush in garden—4 or 5 days in October. Cut roses grown outdoors and kept at living-room temperatures—5 days in October.

*Reproductive organs*

Stamens: From average number to many; arranged regularly about pistils; a few mixed with petaloids.

Filaments: From medium length to long; from 6 mm. to 10 mm. in length; most with anthers. Color—near Orange, Plate 12/1, page 12 (Wilson).

Anthers: From small to medium size; all open approximately at once. Color: upper side—margins near Saffron Yellow, Plate 7, page 7 (Wilson), with remainder near Lemon Yellow, Plate 4/2, page 4 (Wilson); under side—near Lemon Yellow, Plate 4/2, page 4 (Wilson).

Pollen: Abundant. Color—near Saffron Yellow, Plate 7, page 7 (Wilson).

Pistils: Many; approximately 90 in number.

Styles: Moderately even; from short to average length; from 5 mm. to 11 mm. in length; average caliper; bunched. Color—upper ½ of style near Carmine, Plate 21, page 21 (Wilson), with remainder near Primrose Yellow, Plate 601/1, page 65 (Wilson).

Stigma: Color—near Majolica Yellow, Plate 09/1, page 102 (Wilson).

Ovaries: Usually all enclosed in calyx.

Hips: From short to average length; globular; smooth; walls thick and fleshy. Color (one-half mature)—between Courge Green, Plate XVII (Ridgway) and Biscay Green, Plate XVII (Ridgway).

Sepals: Permanent; from medium length to long; curled. Color: inside—between Grape Green, Plate XLI (Ridgway) and Asphodel Green, Plate XLI (Ridgway); outside—between Courge Green, Plate XVII (Ridgway) and Biscay Green, Plate XVII (Ridgway).

Seeds: Few; usually from 4 to 10 in number; usually from small to medium size.

*Plant*

Foliage:

*Leaves.*—Compound of usually 3 to 5 leaflets; from normal abundance to abundant; from medium size to large; leathery and semi-glossy.

*Leaflets.*—Shape—oval, with apex usually acute. Base—round. Margin—simply serrate.

*Color.*—Mature: upper surface—between Deep Dull Yellow-Green (1), Plate XXXII (Ridgway) and Dark Dull Yellow-Green, Plate XXXII (Ridgway); under surface—near Light Grape Green, Plate XLI (Ridgway). Young: upper surface—between Natal Brown, Plate XL (Ridgway) and Olive Brown. Plate XL (Ridgway); under surface—between Mineral Red, Plate XXVII (Ridgway) and Indian Red, Plate XXVII (Ridgway).

*Rachis (the supporting stem of the compound leaf).*—Average size. Upper side—grooved; with many stipitate glands on edges. Under side—usually smooth; sometimes with from 1 to 3 small prickles.

*Stipules.*—Medium length; medium width; with from short to medium length points turning out at an angle of less than 45°.

*Disease resistance.*—Better-than-average resistance to mildew, as compared with other varieties grown under comparable cultural conditions at Ontario, California.

Growth:

*Habit.*—Bushy; upright-spreading; much-branched.

*Growth.*—Very vigorous.

*Canes.*—From medium to heavy caliper.

*Main stems.*—Color—near Rainette Green, Plate XXXI (Ridgway), usually with streaks of near Russet, Plate XV (Ridgway). Large prickles—several; medium length; hooked slightly downward; with medium length, moderately narrow base; color—near Army Brown, Plate XL (Ridgway). Small prickles—very few; color—near Army Brown, Plate XL (Ridgway). Hairs—none.

*Branches.*—Color—between Courge Green, Plate XVII (Ridgway) and Biscay Green, Plate XVII (Ridgway). Large prickles—several; moderately short; hooked slightly downward; with medium length, moderately narrow base; color—near Rood's Brown, Plate XXVIII (Ridgway). Small prickles—few; color—near Rood's Brown, Plate XXVIII (Ridgway). Hairs—none.

*New shoots.*—Color—near Absinthe Green, Plate XXXI (Ridgway), overlaid with near Citrine Drab, Plate XL (Ridgway) on side exposed to the sun. Large prickles—several; medium length; hooked slightly downward; with medium length, narrow base; color—near Prussian Red, Plate XXVII (Ridgway). Small prickles—few; color—near Prussian Red, Plate XXVII (Ridgway). Hairs—none.

I claim:

A new and distinct variety of rose plant of the class between the hybrid tea and floribunda classes, substantially as herein shown and described, characterized particularly as to novelty by the unique combination of a very vigorous, much-branched and fast-breaking plant habit, attractive and disease-resistant foliage of from medium to large size, a floriferousness at least as good as, and probably slightly better than either "Roundelay" (Plant Patent No. 1,280) or "Fandango" (Plant Patent No. 894), a habit of bearing flowers on stems of medium length, with the flowers borne sometimes singly and sometimes in small clusters, an attractive ovoid to urn-shaped bud form, said buds opening to a well-formed, high-centered, double flower of medium petalage, a flower size about equal to that of "Fandango," a better-than-average petal substance, making the flowers quite long-lasting when cut, and a general color tonality of the flowers of light pink on the inner surface of the petals, with dark pink on the reverse surface of the petals.

No references cited.